United States Patent
Manhard et al.

(10) Patent No.: US 12,259,307 B2
(45) Date of Patent: Mar. 25, 2025

(54) METHOD AND MEASURING APPARATUS FOR INVESTIGATING THE HYDROGEN PERMEABILITY OF A TEST OBJECT

(71) Applicant: Max-Planck-Gesellschaft zur Foerderung der Wissenschaften e. V., Munich (DE)

(72) Inventors: Armin Manhard, Garching (DE); Malte Stienecker, Garching (DE); Udo Von Toussaint, Garching (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 239 days.

(21) Appl. No.: 17/922,231

(22) PCT Filed: Apr. 30, 2021

(86) PCT No.: PCT/EP2021/061391
§ 371 (c)(1),
(2) Date: Oct. 28, 2022

(87) PCT Pub. No.: WO2021/224124
PCT Pub. Date: Nov. 11, 2021

(65) Prior Publication Data
US 2023/0175946 A1    Jun. 8, 2023

(30) Foreign Application Priority Data

May 4, 2020   (DE) .................. 102020111959.3

(51) Int. Cl.
*G01N 15/08*   (2006.01)
*G01M 3/22*    (2006.01)
*G01N 33/00*   (2006.01)

(52) U.S. Cl.
CPC ....... *G01N 15/0806* (2013.01); *G01N 33/005* (2013.01); *G01N 2015/0866* (2013.01)

(58) Field of Classification Search
CPC ............. G01N 15/0806; G01N 33/005; G01N 2015/0866; G01N 21/59; G01N 27/128;
(Continued)

(56) References Cited

U.S. PATENT DOCUMENTS 3,768,975 A   10/1973  Toy
5,849,073 A   12/1998  Sakamoto et al.
(Continued)

FOREIGN PATENT DOCUMENTS

DE   102004047427 A1   4/2006
DE   102007043382 A1   3/2009
(Continued)

OTHER PUBLICATIONS

Ngene et al. (2014). Seeing hydrogen in colors: low-cost and highly sensitive eye readable hydrogen detectors. Advanced Functional Materials, 24, 2374-2382.
(Continued)

*Primary Examiner* — Brandi N Hopkins
(74) *Attorney, Agent, or Firm* — Caesar Rivise, PC

(57) ABSTRACT

A method for testing the hydrogen permeability of a test object 1 includes the steps of provision of a sensor device 110 on a first side 3 of the test object 1, application of a test gas 5 including hydrogen 2 to a second side 4 of the test object 1, and detection of permeating hydrogen 2 passing through the test object 1 from the second side 4 to the first side 3 with the sensor device 110, wherein the sensor device 110 includes at least one hydrogen absorbing sensor layer 111 and the detection of the permeating hydrogen 2 including a detection of a change of state of the at least one sensor
(Continued)

layer 111. A measuring apparatus 100 for testing the hydrogen permeability of a test object 1 is also described.

13 Claims, 2 Drawing Sheets

(58) Field of Classification Search
CPC ...... G01N 21/78; G01N 21/75; G01N 21/783; G01N 15/0826; G01N 33/20; G01N 21/553; G01M 3/20; C08K 5/46; G02B 1/10
See application file for complete search history.

(56) References Cited

U.S. PATENT DOCUMENTS

| | | |
|---|---|---|
| 6,519,041 B1 | 2/2003 | Berthold |
| 6,596,236 B2 * | 7/2003 | DiMeo, Jr. ............ G01N 21/783 73/31.06 |
| 8,646,315 B2 | 2/2014 | Wetzig |
| 8,752,412 B2 | 6/2014 | Wetzig et al. |
| 8,758,691 B2 | 6/2014 | Uchiyama et al. |
| 9,810,597 B2 | 11/2017 | Hilgers et al. |
| 2002/0017126 A1 | 2/2002 | Dimeo, Jr. et al. |
| 2003/0153088 A1 | 8/2003 | Dimeo, Jr. et al. |
| 2007/0111313 A1 | 5/2007 | Saloka |
| 2008/0262757 A1 | 10/2008 | Yokosawa et al. |
| 2011/0171066 A1 | 7/2011 | Captain et al. |

FOREIGN PATENT DOCUMENTS

| | | |
|---|---|---|
| DE | 102007057944 A1 | 6/2009 |
| DE | 102013218506 A1 | 3/2015 |
| EP | 0936465 A2 | 8/1999 |
| GB | 2454879 A | 5/2009 |
| JP | 2004093162 A | 3/2004 |

OTHER PUBLICATIONS

Wang et al. (2017). Hydrogen sensor based on palladium-yttrium alloy nanosheet. Materials Chemistry and Physics, 194, 231-235.

* cited by examiner

METHOD AND MEASURING APPARATUS FOR INVESTIGATING THE HYDROGEN PERMEABILITY OF A TEST OBJECT

CROSS-REFERENCE TO RELATED APPLICATIONS

This application is a U.S. National Phase Application of PCT/EP2021/061391, filed Apr. 30, 2021, which claims priority to DE 102020111959.3 filed May 4, 2020, the contents of which applications are incorporated herein by reference in their entireties for all purposes.

BACKGROUND OF THE INVENTION

The invention relates to a method for investigating the hydrogen permeability of a test object. The invention also relates to a measuring apparatus for investigating the hydrogen permeability of a test object. Applications of the invention are available, for example, with investigating and/or monitoring of materials, for example of containers or conduits for fluids or gases, and/or in materials science.

It is generally known that, in order to test objects for tightness, for example to test for leaks in vessel walls, to investigate their transmissibility (i.e. their permeability) to test gases. Hydrogen and helium in particular are used as test gases due to their low detection limit and the fact that they are relatively inexpensive. To date, the following techniques in particular have been used for testing tightness.

From EP 936 465 A2, a measuring method for determining the hydrogen permeability of a metal sample is known. In this case, a front side of the metal sample is exposed to hydrogen by means of a proton-conducting solid-state electrolyte by applying a voltage, and an electrical measuring value is detected on a rear side of the metal sample by means of a proton- or oxygen-ion-conducting contact in the form of a solid-state electrolyte. The hydrogen permeability of the metal sample can be derived from the measuring electrical value.

In the technique described in DE 10 2007 057 944 A1, a test specimen filled with test gas is inserted into an evacuable test chamber. The test gas leaking out of the test specimen forms a gas mixture with a carrier gas in the test chamber and can be detected using a test gas sensor.

DE 10 2007 043 382 A1 and DE 10 2013 218 506 A1 each disclose a sniffer leak detector which aspirates a test gas diffusing through a test specimen by generating a vacuum and identifies the test gas concentration by means of a test gas sensor and an analysis unit, and determines a leak rate from this test gas concentration.

The above-mentioned tightness testing techniques generally have the disadvantage that they require complex and cost-intensive apparatuses. Furthermore, these techniques are limited to momentary tightness tests, but are not suitable for permanent, in particular continuous, monitoring of the tightness of an object. Finally, another disadvantage is the limited possibility of carrying out spatially resolved measurements. For example, in the methods of EP 0 936 465 A2, DE 10 2007 043 382 A1 and DE 10 2013 218 506 A1, the measurement would have to be repeated successively at different points of the test object in order to be able to make a position-dependent statement about the tightness of the test object. Furthermore, position dependency can only be determined laterally and not, e.g. in the thickness direction of the examined material. With the measuring method of DE 10 2007 057 944 A1 it is not at all possible to say at which positions on the test object test gas leaks out.

Furthermore, solid-state sensors are known that are used to detect hydrogen gas in the ambient air. These solid-state sensors are characterized by a hydrogen-sensitive sensor layer applied to a substrate which sensor layer changes one of its physical properties when it absorbs hydrogen and can indicate, for example by a change in color, that hydrogen gas is present in the ambient air.

For example, US 2003/0153088 A1 describes a sensor with a sensor layer comprising a rare earth metal and with a micro-heating plate structure for selectively heating the sensor layer. Heating the sensor layer results in improved sensor properties, wherein the absorption of hydrogen, for example, causes a change in the optical properties of the sensor layer from opacity to transparency. From U.S. Pat. No. 8,758,691 B2, a sensor with a sensor layer comprising an Mg—Ni-based alloy and a Zr—Ti-based alloy, and catalyst layers capable of accelerating the hydrogenation of the sensor layer is known. Here, too, the absorption of hydrogen leads to a visually perceptible transparency of the sensor layer.

A sensor layer made of a palladium-yttrium alloy is described by B. Wang et al. in "Materials Chemistry and Physics", 2017, vol. 194, p. 231. The electrical resistance depends on the hydrogen concentration in the environment, so that hydrogen can be detected by measuring the electrical resistance of the sensor layer. In "Advanced Functional Materials", 2014, vol. 24, p. 2374, P. Ngene et al. describe a sensor with a sensor layer made of a thin yttrium layer and with a thin palladium film for hydrogenation or dehydrogenation of the sensor layer. Depending on the absorption of hydrogen, the yttrium reacts to form $YH_{1.9}$, $YH_{2.1}$ und $YH_3$, with the different hydrides exhibiting different optical properties in the form of different shades of grey-blue.

Since odorless and colorless hydrogen gas is easily flammable and forms a highly explosive gas mixture with air, and furthermore inhalation of hydrogen gas can be injurious to health, known solid-state sensors are used to detect hydrogen gas in the environment, for example as a safety precaution. For example, US 2003/0153088 A1describes a solid state sensor provided in a portable device. In the event of a change in the properties of the sensor layer of the solid state sensor, a signal is generated to warn the user that hydrogen gas is present in the ambient air.

In contrast to the above-mentioned tightness tests, in which hydrogen gas is deliberately released locally as a test gas and should be detected with high precision, the solid-state sensors are intended in particular for rapid hydrogen detection in an environment, typically with relatively high detection limits.

The objective of the invention is to provide an improved method of tightness testing and, in particular, a method of investigating the hydrogen permeability of a test object, avoiding disadvantages of conventional techniques. In particular, the method should be simpler and more cost-effective to use than conventional tightness tests, be suitable for permanently, in particular continuously, investigating or monitoring the hydrogen permeability of the test object, and/or improve investigating with spatial resolution. It is also the objective of the invention to provide an improved measuring apparatus for tightness testing and, in particular, for investigating the hydrogen permeability of a test object, avoiding the disadvantages of conventional measuring apparatuses, which in particular is characterized by a simple and cost-effective design and/or simple operation and/or which is suitable for permanent operation and/or simplifies measurement with spatial resolution. Furthermore, the invention is intended to allow new applications of tightness testing on test objects.

These objectives are solved by a method and a measuring apparatus of the invention for investigating the hydrogen permeability of a test object.

BRIEF SUMMARY OF THE INVENTION

According to a first general aspect of the invention, the above objective is solved by a method for investigating the hydrogen permeability of a test object, wherein a sensor device is provided on a first side of the test object and a test gas including hydrogen is applied to a second side of the test object. The terms "first side" and "second side" refer to mutually opposite sections of the test object, which are separated from each other by solid material of the test object, such as a wall material of a vessel or conduit or a material sample. The test object can have any thickness and shape and be made of any solid material. Hydrogen permeability is tested with the sensor device by detecting permeating hydrogen passing through the test object from the second side to the first side. Hydrogen permeability refers to the permeability of the test object to hydrogen molecules of the test gas.

According to the invention, the sensor device comprises at least one hydrogen-absorbing sensor layer. The at least one sensor layer is in direct contact with the material of the test object. The sensor layer can be plane or curved, depending on the shape of the test object and the position of the sensor layer. Due to a reaction of hydrogen with the sensor layer, the sensor layer undergoes a change of state, such as a change of physical and/or chemical properties. The change of state is detectable, for example it is visible and/or measurable, on the basis of at least one property of the sensor layer. Detection of the permeating hydrogen comprises detecting the change of state of the sensor layer in response to the absorption of hydrogen in the sensor layer. As a result, the investigating of hydrogen permeability provides qualitative information about whether hydrogen has reached the sensor layer from the second side and/or quantitative information about the amount of hydrogen passing through to the sensor layer.

According to a second general aspect of the invention, the above objective is solved by a measuring apparatus for investigating the hydrogen permeability of a test object. The measuring apparatus comprises a sensor device and a test gas source. The sensor device is arranged to detect hydrogen on a first side of a test object. The test gas source serves to apply a test gas including hydrogen to a second side of the test object lying opposite the first side. According to the invention, the sensor device comprises at least one hydrogen-absorbing sensor layer, which is adapted to undergo a change of state in response to the absorption of hydrogen. Furthermore, an analysis device optionally may be provided to detect the change in state of the at least one sensor layer. The measuring apparatus is preferably configured to carry out the method according to the first general aspect of the invention or one of its embodiments.

The method and apparatus according to the invention represent substantially simplified techniques compared to conventional tightness tests. For example, the sensor device may consist of one single hydrogen-sensitive sensor layer whose state changes when hydrogen is absorbed and which can directly indicate to the user that hydrogen has passed through at least the section of the test object where the sensor layer is located. By detecting a change of state, it can be determined in particular that the test object is not hydrogen-impermeable between the first and the second sides. Detection can be in-situ, in real-time and non-destructive.

Furthermore, in contrast to known solid-state sensors, the at least one hydrogen-absorbing sensor layer is not applied to an additional substrate for absorbing hydrogen from the ambient air via an exposed side. Rather, the object to be investigated forms a substrate on which the at least one sensor layer according to the invention is disposed.

According to preferred embodiments of the invention, the at least one sensor layer comprises a metal or a chemical compound that reacts with the absorbed hydrogen and thereby causes the change of state of the sensor layer. Preferred sens or layer materials are the metal yttrium and the chemical compound tungsten trioxide. Other metals are, for example, hafnium and magnesium. The advantages of the above-mentioned materials are in particular the high sensitivity of the sensor layer.

According to further preferred embodiments of the invention, the at least one sensor layer is preferably a thin film, for example with a thickness in the range of 15 nm to 100 nm.

Depending on the selected metal or chemical compound, different types of state changes can occur, at least one of which is detected. According to a first variant, the change of state may comprise a change in the optical properties of the at least one sensor layer, preferably a color change. Advantageously, the color change (in particular the change in spectral reflectivity) can be detected and/or monitored particularly easily. For example, the color change can be detected by the user with the naked eye. Alternatively or additionally, the color change can be captured with a camera and/or a light microscope. Other ways of detecting the color change are ellipsometric measurements.

Alternatively or additionally, the detected change of state may comprise a structural change of the at least one sensor layer. The structural change can be, for example, a change in the density of the sensor layer material, which can be captured with an electron microscopy device. Investigating of the hydrogen permeability based on the change in density of the sensor layer material has particular advantages when investigating objects with especially small dimensions, for example in the sub-µm range.

According to a further alternative or in addition to the variants mentioned, the detected change of state may comprise a change of at least one electrical property of the at least one sensor layer, for example electrical conductivity or electrical resistance. This change of state can be detected, for example, by a current measurement at the at least one sensor layer using a current measuring device.

In many applications of the invention, qualitative information as to whether hydrogen has reached the sensor layer from the second side may be sufficient for investigating the hydrogen permeability of the test object. If, according to a further embodiment of the invention, the detection of permeating hydrogen includes a quantitative assessment of the hydrogen, additional advantages can be obtained with regard to the characterization of hydrogen permeability. For example, a degree of material fatigue or embrittlement can be determined. For the quantitative assessment of the hydrogen, the material of the at least one sensor layer is chosen in such a way that different amounts of permeating hydrogen absorbed by the sensor layer lead to quantitatively and/or qualitatively different changes of state in the sensor layer. For example, the detector layer may comprise a metal such as yttrium, wherein the metal can form different chemical compounds with the hydrogen depending on the amount of hydrogen present. These chemical compounds are characterized by different optical properties. For example, a camera can be used to detect a change in color which, depending on the color detected, provides a quantitative indication of the amount of hydrogen that has passed through the test object.

According to a further, particularly advantageous embodiment of the invention, the permeating hydrogen can be detected with spatial resolution. This makes it possible to test different sections of the test object and locate possible leaks. Assessment of hydrogen permeation with spatial resolution, that is to say, simultaneous detection at several positions on the test object, represents a significant advantage of the invention. Spatially resolved measurements are not possible with known leak tightness tests, or are only possible sequentially in time. Advantageously, different variants exist for carrying out spatially resolved detection.

According to a first variant, the sensor device comprises a plurality of sensor layers disposed at distances from one another at different positions on the first side of the test object. The sensor layers can be disposed individually at different positions on the test object, for example in a row-configuration or matrix-configuration, in order to determine the positions in the material of the test object where hydrogen is able to pass through via the response of individual sensor layers, that is to say, by detecting the change in state of the individual sensor layers. Accordingly, spatial resolution of the detection of permeating hydrogen can be achieved by detecting the permeating hydrogen at the different positions.

Alternatively or additionally, according to a further variant, the at least one sensor layer can be divided into individual structural elements (or: sensor elements) between which hydrogen exchange is prevented, that is to say, restricted or excluded, laterally within the layer. When hydrogen gas is absorbed in a structural element of the sensor layer, distribution of the absorbed hydrogen into neighboring structural elements is prevented. Division of the sensor layer into individual structural elements has the particular advantage that hydrogen permeability can be detected with increased resolution depending on the dimension of the structural elements. The division of the sensor layer can also increase sensitivity due to the fact that individual structural elements reach the change of state sooner and provide high spatial resolution even with long application times.

To provide the structural elements, the material of the sensor layer is chosen so that the structural elements can be produced in a structured manner. The structural elements can be formed additively by local material deposition or subtractively by local material removal from a closed layer. Various methods are available to apply the structural elements to the test object, for example through suitable mask systems, lithography methods or vapor deposition. The structural elements may preferably comprise discrete pixels or discrete lines (for example, rectangles). Accordingly, the spatial resolution of detection of permeating hydrogen can be achieved by detecting the permeating hydrogen in the individual structural elements.

The resolution, that is to say, the accuracy of the spatial resolution, depends on the size of the sensor layers used or the size of the structural elements and the distance between the sensor layers or structural elements. A high spatial resolution can be achieved, for example, by discrete pixels with characteristic dimensions in the range of approx. 10 nm to 100 µm. A lower spatial resolution, for example in the cm, dm or m range, can be realized by using a large number of sensor layers or structural elements, wherein simultaneous investigating of correspondingly extended large areas and diverse geometries of the test object is allowed.

Spatially resolved detection of permeating hydrogen with a sensor layer divided into individual structural elements makes it possible to verify a local occurrence of hydrogen two-dimensionally, that is to say, resolved in the areal extent of the at least one sensor layer. This allows regions with high permeation to be distinguished from those with lower permeation. Because hydrogen accumulates in the at least one sensor layer, even extremely low permeation rates can be examined given sufficiently long application of hydrogen.

To increase the adhesion of the sensor device to the first side of the test object, according to a further embodiment, the test object, in particular at least the first side of the test object, is cleaned by surface sputtering, preferably with argon ions, before the sensor device is provided (that is to say, before the at least one sensor layer is applied to the first side of the test object).

According to a further embodiment, the at least one sensor layer of the sensor device is applied to the first side of the test object by a coating process, preferably thin-film deposition. The thin-film deposition can, for example, comprise electron beam evaporation in an ultra-high vacuum. The use of a coating process has the advantage that the design of the sensor device can be adapted particularly easily to the test object.

The invention is not limited to applying the sensor device directly to the first side on the surface of the test object and carrying out tests there. Alternatively or additionally, it is possible to test hydrogen permeability within the test object, that is to say, in the thickness direction in the material between the first and the second sides of the test object. For this purpose, provision of the sensor device according to a preferred embodiment comprises embedding the at least one sensor layer in the material on the first side of the test object. To detect the permeating hydrogen, the at least one sensor layer is exposed by material removal and the change of state of the exposed sensor layer is assessed. Due to the material removal, this test is destructive and can therefore only be used for single measurements.

According to a particularly preferred variant of the measurement in the material, not only one sensor layer, but a plurality of sensor layers are embedded at different depths at the first side of the test object. For example, sensor layers and layers of the test object can be applied alternately one above the other. This makes it possible not only to test the hydrogen permeability of the test object in one plane, but also to obtain a depth profile of the hydrogen permeability. To determine the depth profile, after the test gas has been applied to the second side of the test object, the sensor layers are successively exposed using electrochemical methods, for example. The change of state to be detected is determined at each exposed sensor layer.

It is thus advantageously possible, by means of the method and the measuring apparatus according to the invention, to determine the hydrogen permeability at a specific depth or to obtain a depth profile at a plurality of depths of the test object. This possibility is not offered by known tightness tests, which can only determine whether hydrogen escapes from a surface of the test object.

When according to a further advantageous embodiment of the invention it is provided that the sensor device absorbs hydrogen exclusively from the material of the test object, falsification of the test due to absorption of hydrogen from the environment of the test object is avoided in an advantageous manner. For this purpose, the at least one sensor layer preferably has a cover layer impermeable to hydrogen on a side of the sensor device facing away from the test object. For example, the at least one sensor layer is covered with the hydrogen-impermeable cover layer after it has been applied to the test object. The cover layer can, for example, comprise an oxide layer, preferably yttrium oxide, which is formed when the sensor layer comes into contact with air or is deposited using a thin-film process. Alternatively or additionally, gold can be used, which is applied by electron beam evaporation, for example.

Advantageously, the cover layer can fulfil a dual function. First, as described above, it can act as a barrier against ambient hydrogen. Second, it can protect the sensor device against chemical environmental influences, so that the sensor device can be used in freely selectable environments, for example in a high vacuum, in atmospheric air and/or in wet chemical media.

Advantageously, the invention offers a wide range of applications. For example, the method can be carried out for a non-destructive monitoring of components, such as gas pipelines, whose stability could be affected by hydrogen permeability. Potential damage spots could thus be detected at an early stage and repaired as a precautionary measure. Furthermore, detection of hydrogen permeability according to the invention can be used, for example in research and development, to investigate the causes of hydrogen embrittlement. Moreover, the invention can be used for leak searching, for example in evacuated containers or vacuum systems. In processes using hydrogen (hydrogen technology), the invention provides a sensor for hydrogen gas leaks.

BRIEF DESCRIPTION OF THE DRAWINGS

Further details and advantages of the invention are described in the following with reference to the accompanying drawings. These show schematically.

DETAILED DESCRIPTION OF PREFERRED EMBODIMENTS OF THE INVENTION

Embodiments of the invention are described below with exemplary reference to a sensor device with a plurality of yttrium-based sensor layers or a structured yttrium-based sensor layer. It is emphasized that implementation of the invention is not limited to these variants, but rather use can be made of other sensor devices of different designs, for example with sensor layers and/or structural elements with other sizes, shapes, arrangements and/or materials, such as tungsten trioxide. The test object can have any thickness and shape, and may also be made of any material of freely selectable choice, provided that a surface of the test object can be coated with the at least one sensor layer. In particular, variations of the dimensions of the sensor device are possible, so that it can be adapted to a specific application, for example. Details of the color or structure detection, using a camera, microscope or electron microscope, for example, are not described here, as these are known from conventional techniques.

Figure 1:
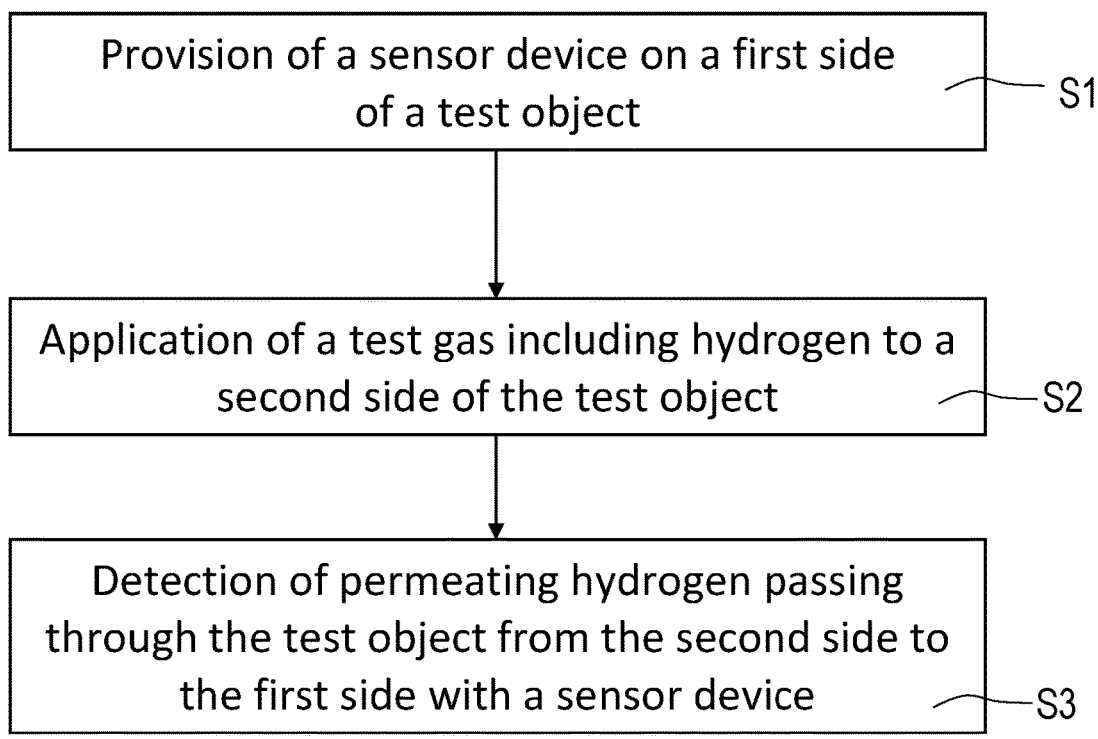
FIG. 1: a representation of the method according to the invention for investigating the hydrogen permeability of a test object.

With steps S1 to S3, FIG. 1 schematically shows the method according to the invention for investigating the hydrogen permeability of a test object. In step S1, the sensor device is provided on the first side of the test object, wherein the sensor device comprises at least one hydrogen-absorbing sensor layer. The at least one sensor layer can be applied to the surface of the first side or embedded in the material of the test object on the first side.

Provision of the sensor device comprises, for example, thin film deposition of the at least one sensor layer on a surface forming the first side of the test object. Optionally, this step can be preceded by cleaning of the test object by surface sputtering.

In step S2, a test gas containing hydrogen is applied to the second side of the test object. The test gas comprises, for example, hydrogen, which is passed over the surface on the second side of the test object lying opposite the sensor device.

In step S3, permeating hydrogen passing through the test object from the second side to the first side is detected with the sensor device. This detection comprises a detection of a change of state of the sensor layer. The change of state may comprise a color change or structural change of the at least one sensor layer, wherein the detection of the color change being carried out, for example, visually or with a camera or optical microscope, and the detection of the structural change being carried out, for example, with an electron microscope.

Detection can be done directly by detecting the change of state of the sensor device applied to the first side. If the sensor layer is embedded in the material of the first side of the test object, the sensor layer is first exposed by material removal.

Detection at step S3 may also comprise a quantitative assessment of the permeating hydrogen. For this purpose, the at least one sensor layer can be configured in such a way that different amounts of permeating hydrogen in the at least one sensor layer lead to different or differently pronounced changes of state.

Detection according to step S3 can further be carried out with spatial resolution. For this purpose, a spatially resolving sensor device is provided in step S1, wherein a plurality of sensor layers being disposed at distances from one another at different positions and/or depths on the first side of the test object, and/or the at least one sensor layer being structured so as to form individual structural elements. The spatial resolution of detection of the permeating hydrogen is achieved by detecting the permeating hydrogen at the different positions and/or depths and/or at the structural elements.

Figure 2:
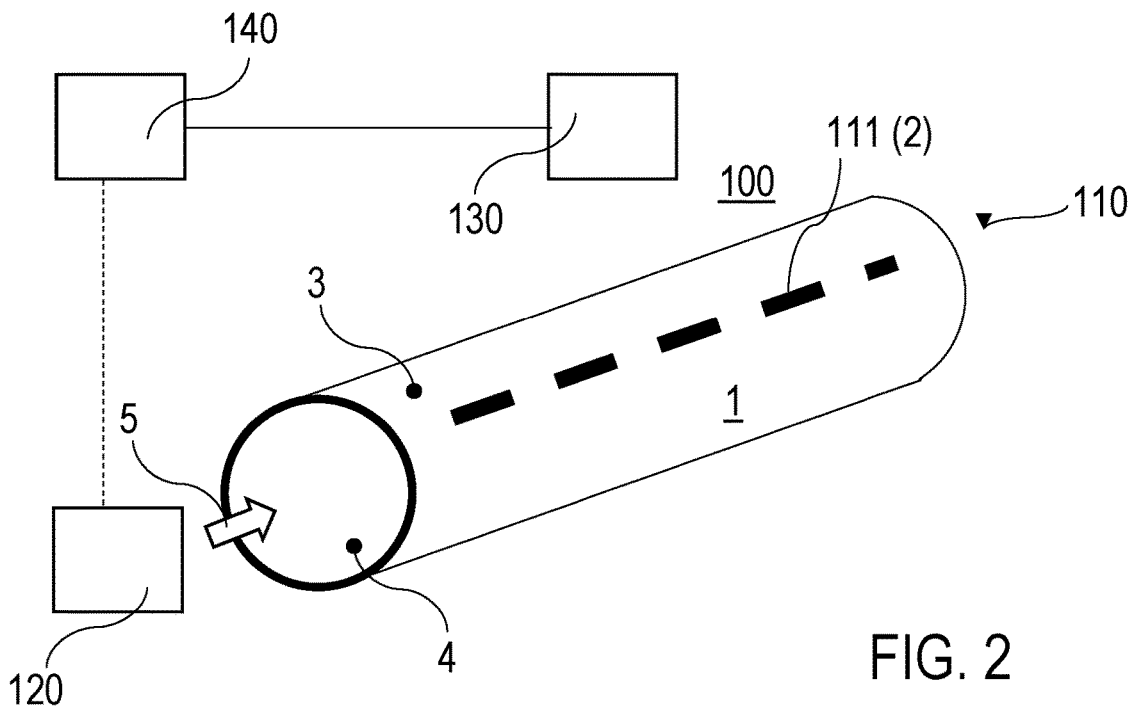
FIG. 2: an illustration of an embodiment of the measuring apparatus according to the invention.

FIG. 2 schematically illustrates an optical detection of hydrogen permeability using the example of a tubular test object 1, and components of an embodiment of the measuring apparatus 100 according to the invention. The test object 1 is, for example, a steel pipe of a vacuum system or of a chemical production plant whose wall is to be tested. The method according to the invention can be carried out with the open configuration of the test object 1 shown in FIG. 2 or alternatively on a closed system in which the test object 1 is evacuated, apart from the supply of test gas.

The measuring apparatus 100 comprises a sensor device 110, a test gas source 120 and an analysis device 130. The sensor device 110 is formed by a series of sensor layers 111 disposed on a first side 3 (here, for example, the outer surface) of the test object 1. The sensor layers 111 consist, for example, of yttrium with a thickness of 50 nm deposited on the first side 3. Each sensor layer 111 has an extension of, for example, 1 mm*1 mm, and the sensor layers 111 are distributed over a length of a few decimeters to a few meters on the first side 3. Alternatively, the sensor layers 111 may have an extension of, for example, 1 mm*10 mm or 10 mm*10 mm.

The test gas source 120 comprises a test gas reservoir, a control element such as a control valve, and a supply line (details not shown) through which the test gas 5, for example a hydrogen-air mixture, is supplied in order to be applied to the second side 4 (here, for example, the inner surface) of the test object 1.

The analysis device 130 is, for example, a color-sensitive camera whose field of view covers the sensor layers 111. The analysis device 130 is connected to or equipped with a control and evaluation device 140 which evaluates image signals from the camera and detects color changes of the sensor layers 111. When the sensor layers 111 accumulate hydrogen 2 which is supplied internally with the test gas 5 and has passed through the wall material of the test object 1, a color change occurs, for example from light grey to dark blue. The control and evaluation device 140 may also be connected to the test gas source 120, for example in order to control the control element for the test gas supply.

Figure 3:
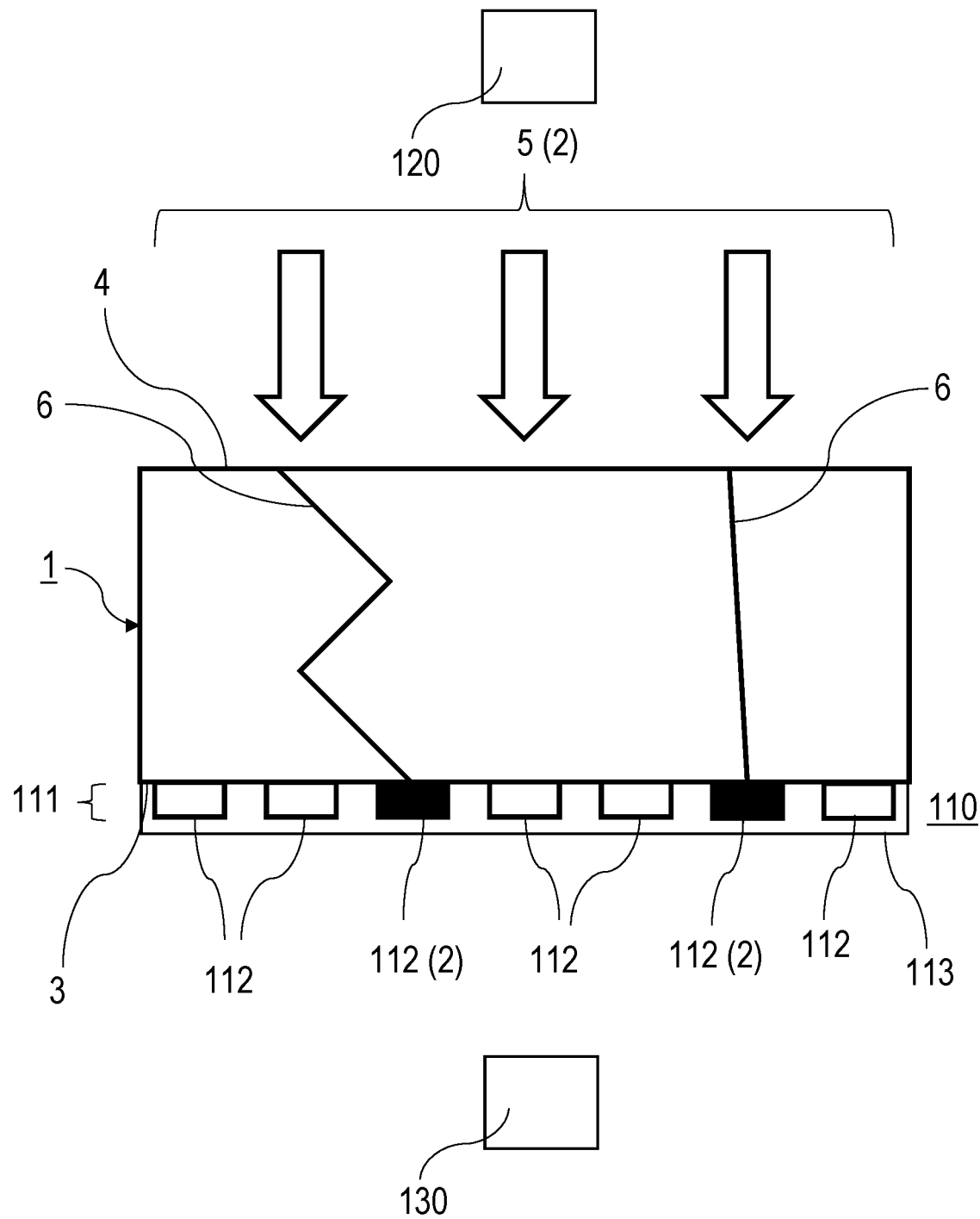
FIG. 3: an illustration of an optical detection of the hydrogen permeability of a test object according to an embodiment of the method according to the invention.

FIG. 3 shows a further application of the invention for investigating a test object 1 in the form of a thin foil, for example of tungsten, with a thickness of 50 µm, for example. A sectional view of the foil is shown with a first side 3, on which the sensor layer 110 is disposed, and a second side 4. When the method is carried out, the second side 4 is exposed to the test gas 5 containing hydrogen 2.

On the first side 3 of the test object 1, the sensor device 110 is applied in the form of a sensor layer 111, which comprises individual structural elements 112, such as discrete pixels. The structural elements 112 consist, for example, of yttrium (Y) thin films. The structural elements 112 are covered with a schematically shown cover layer 113 of yttrium oxide, for example.

A test gas 204 including hydrogen is applied to the second side 4 of the test object 1 from a schematically shown test gas source 120. The hydrogen 2 penetrates the second side 4 and diffuses through the material of the test object 1. Grain boundaries 6 capture the diffusing hydrogen 2 and pass it through to the first side 3 of the test object 1. Only those pixels of the structural elements 112 that meet grain boundaries 6 become saturated with hydrogen 2 and change their color through the formation of yttrium hydride (YH2). This color change can be detected with a schematically shown analysis device 130, such as an optical microscope, and shows the horizontally (that is to say, two-dimensionally) resolved distribution of the hydrogen permeation and also, based on the intensity of the coloring, the amount of hydrogen 2 that has permeated through the material. With this application of the invention, it is thus possible to determine where grain boundaries 6 are located and how much hydrogen 2 they have transported, that is to say, what dimensions the grain boundaries 6 have.

With the embodiments shown in FIGS. 2 and 3, regions of high permeation can be distinguished from those of lower permeation. Because of accumulation of hydrogen in the sensor layer 110, even extremely low permeation rates can be tested given sufficiently long exposing times to hydrogen. The structuring of the sensor layer 110 prevents hydrogen from being distributed between neighboring structural elements 112. The methods can be carried out in situ, in real-time and non-destructively, depending on the specific application. To produce a depth profile on a thicker material, sample removal would be carried out to expose buried sensor layers and determine their change of state.

The features of the invention disclosed in the foregoing description, the drawings and the claims may be significant, both individually and in combination or sub-combination, for the realization of the invention in its various embodiments.

The invention claimed is:

1. A method for testing a hydrogen permeability of a test object, comprising the following steps:
   provision of a sensor device on a first side of the test object,
   application of a test gas including hydrogen to a second side of the test object, and
   detection of permeating hydrogen passing through the test object from the second side to the first side with the sensor device, wherein:
   the sensor device comprises at least one hydrogen-absorbing sensor layer,
   the detection of the permeating hydrogen comprises a detection of a change of state of the at least one sensor layer, and
   the permeating hydrogen is detected with spatial resolution.

2. The method according to claim 1, wherein
   different amounts of permeating hydrogen absorbed by the at least one sensor layer lead to different changes of state in the at least one sensor layer, and
   the detection of the permeating hydrogen comprises a quantitative assessment of the permeating hydrogen.

3. The method according to claim 1, wherein
   the at least one sensor layer is divided into individual structural elements, so that, when hydrogen is absorbed in a structural element, the absorbed hydrogen is prevented from being distributed to neighboring structural elements, and
   the spatial resolution of detection of permeating hydrogen is achieved by detecting the permeating hydrogen at the structural elements.

4. The method according to claim 1, wherein
   the change of state comprises a change of color of the at least one sensor layer, and
   the change of state is detected with at least one of a camera and an optical microscope.

5. The method according to claim 1, wherein
   the change of state comprises a structural change of the at least one sensor layer, and
   the change of state of the at least one sensor layer is detected with an electron microscopy device.

6. The method according to claim 1, further comprising the step of
   cleaning the test object by surface sputtering.

7. The method according to claim 1, wherein
   the provision of the sensor device comprises a thin film deposition of the at least one sensor layer on a surface forming the first side of the test object.

8. The method according to claim 1, wherein
   the provision of the sensor device comprises embedding the at least one sensor layer in the first side of the test object, and
   the detection of the permeating hydrogen comprises exposing the at least one sensor layer by material removal and detecting the change of state of the exposed sensor layer.

9. The method according to claim 8, wherein
   the provision of the sensor device comprises embedding a plurality of sensor layers at different depths in the first side of the test object, and a depth profile of the hydrogen permeability is obtained by step-wise exposing the sensor layers and detecting the changes of state of the exposed sensor layers.

10. The method according to claim 1, wherein the sensor device comprises at least one of the following features:
the at least one sensor layer comprises at least one metal or a chemical compound, and
on a side of the sensor device facing away from the test object, the sensor layer has a hydrogen-impermeable cover layer.

11. The method according to claim 1, with a step of
assessment of hydrogen embrittlement and/or a damage spot in the test object, wherein hydrogen has been detected with the sensor device.

12. The method according to claim 1, wherein
the sensor device comprises a plurality of sensor layers disposed at distances from one another at different positions on the first side of the test object, and
the spatial resolution of detection of the permeating hydrogen is achieved by detecting the permeating hydrogen at the different positions.

13. A measuring apparatus for testing a hydrogen permeability of a test object, comprising:
a sensor device disposed to detect hydrogen on a first side of a test object, and
a test gas source for applying a test gas including hydrogen to a second side of the test object lying opposite the first side, wherein
the sensor device comprises at least one hydrogen-absorbing sensor layer which is configured to undergo a change of state in response to the absorption of hydrogen, and
an analysis device is provided whereby the change of state of the at least one sensor layer can be detected.

* * * * *